(12) United States Patent
Ricci et al.

(10) Patent No.: US 6,387,327 B1
(45) Date of Patent: May 14, 2002

(54) APPARATUS FOR THE PREPARATION AND THE PERFORMANCE OF SEDIMENTATION VELOCITY TESTS ON ORGANIC LIQUIDS AND OTHER SUBSTANCES

(75) Inventors: Antonio Ricci, Monteriggioni; Francesco Cocola, Sovicille, both of (IT)

(73) Assignee: Diesse Diagnostica Senese S.R.L. (IT)

(*) Notice: Subject to any disclaimer, the term of this patent is extended or adjusted under 35 U.S.C. 154(b) by 0 days.

(21) Appl. No.: 09/194,088
(22) PCT Filed: May 13, 1997
(86) PCT No.: PCT/IT97/00110
  § 371 Date: Nov. 9, 1998
  § 102(e) Date: Nov. 9, 1998
(87) PCT Pub. No.: WO97/43621
  PCT Pub. Date: Nov. 20, 1997

(30) Foreign Application Priority Data

May 16, 1996 (IT) .......................... FI96A0115

(51) Int. Cl.$^7$ .......................... G01N 33/80; G01N 21/13
(52) U.S. Cl. .......................... 422/72; 73/61.66; 422/63; 422/64; 422/67; 422/104; 436/43; 436/45; 436/47; 436/48; 436/70; 436/165; 436/177; 494/7; 494/11; 494/16
(58) Field of Search ............................. 422/63, 64, 67, 422/104, 72; 436/43, 45, 47, 48, 165, 177, 70; 494/7, 11, 16, 47, 84; 73/61.66, 61.68, 61.69

(56) References Cited

U.S. PATENT DOCUMENTS

| | | | | |
|---|---|---|---|---|
| 3,163,404 A | * | 12/1964 | Kraft et al. | 494/16 X |
| 3,199,775 A | * | 8/1965 | Drucker | 494/19 |
| 3,401,876 A | * | 9/1968 | Lucas | 494/16 |
| 3,614,434 A | * | 10/1971 | Horwitz et al. | 422/64 X |
| 3,980,227 A | * | 9/1976 | Witty et al. | 494/7 |
| 4,435,167 A | * | 3/1984 | Stower | 494/16 |
| 4,475,411 A | * | 10/1984 | Wellerfors | 422/64 X |
| 4,479,720 A | * | 10/1984 | Mochida et al. | 366/214 |
| 4,774,056 A | * | 9/1988 | Ricci et al. | 436/70 X |
| 5,045,047 A | * | 9/1991 | Hutchins et al. | 494/17 |
| 5,133,208 A | * | 7/1992 | Ricci | 73/61.66 |
| 5,367,157 A | * | 11/1994 | Nilsson et al. | 250/231.13 |
| 5,827,746 A | * | 10/1998 | Duic | 436/70 |

OTHER PUBLICATIONS

T. Dschietzig et al, Biomed. Technik 1994, 39, 8–12.*

M. Castaneda et al, Anal. Biochem. 1971, 44, 381–387, Dec. 1971.*

* cited by examiner

*Primary Examiner*—Arlen Soderquist
(74) *Attorney, Agent, or Firm*—McGlew and Tuttle, P.C.

(57) ABSTRACT

On a base structure (101, 103), an assembly (104) oscillates about a horizontal axis (X—X) between two limit positions; on said assembly, a rotor (106) is capable of rotating about an axis (Y—Y) of rotation orthogonal to said horizontal axis (X—X) and has a ring of seats (121) for test tubes (1); an actuator (145) moves said assembly into a position with the axis of rotation (Y—Y) roughly horizontal, to carry out an agitation stage, and into a position with the axis of rotation (Y—Y) vertical, to carry out, before the reading stage, a centrifugation stage. The ring of seats (121) for test tubes has the test tubes (1) oriented, in the vertical position of said axis of rotation (Y—Y), with their bottom facing downwards and outwards.

19 Claims, 8 Drawing Sheets

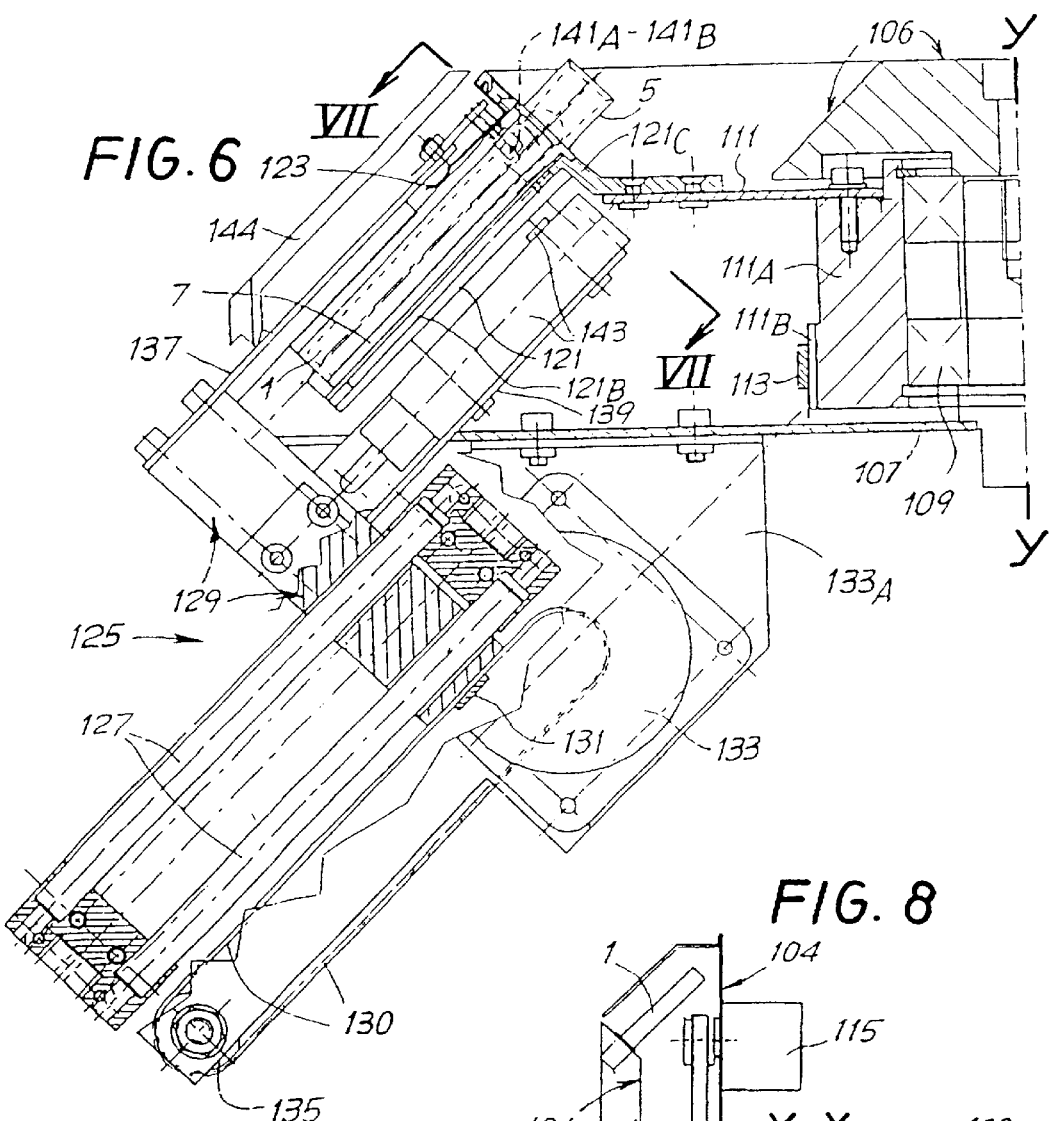
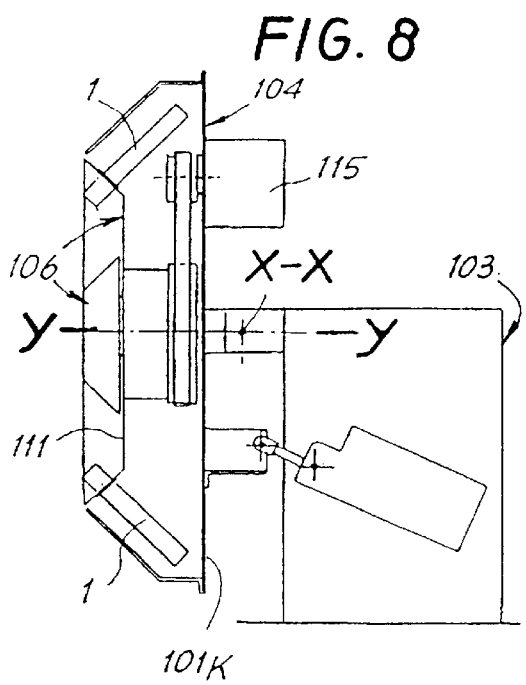
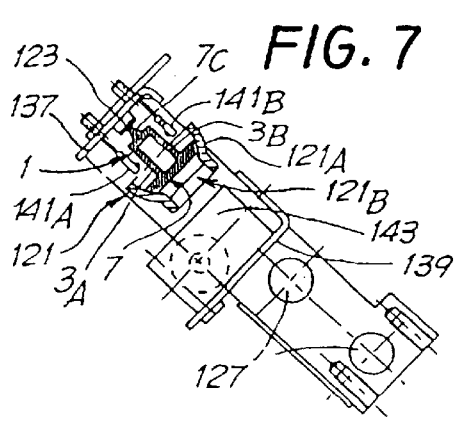

US 6,387,327 B1

APPARATUS FOR THE PREPARATION AND THE PERFORMANCE OF SEDIMENTATION VELOCITY TESTS ON ORGANIC LIQUIDS AND OTHER SUBSTANCES

DESCRIPTION

1. Technical Field

The invention relates to an apparatus for the preparation and the performance of sedimentation velocity tests on previously treated organic liquids which have to be agitated in containers of test-tube type, such as the so-called E.S.R. Erytro Sedimendation Rate, and for similar uses.

2. Background Art

Such an apparatus is known from, for example, Italian Patent No. 1,233,510 and from the corresponding European Patent Publication No. 391,861 (Appl. No. 90830094.0); in the apparatus described therein, the sedimentation of the preparation takes place by means of gravity alone, and has relatively long analysis times. Such an apparatus comprises: an assembly, on a base structure, which assembly oscillates about a horizontal oscillation axis between two limit positions, a rotor, on said assembly, which rotor is capable of rotating about an axis of rotation orthogonal to said horizontal axis, a ring of seats for test tubes on said rotor, each seat being arranged and oriented symmetrically about said axis of rotation with an inclination in relation to said axis of rotation in the respective diametral plane. The apparatus also comprises means of moving said assembly into a position with the axis of rotation of the rotor roughly horizontal, to carry out an agitation stage, and into a position with the axis of rotation vertical, to carry out a reading stage. Means are provided, in a reading station, for optical reading along the test tube, when this test tube arrives in the reading station by intermittent movements of said rotor when it is arranged with the axis of rotation oriented upwards.

OBJECTS AND DISCLOSURE OF THE INVENTION

The aim of the invention is to shorten the time necessary for carrying out a cycle of operations (which is slowed down mainly by the stage of sedimentation by gravity) in an apparatus of the abovementioned type.

According to the invention, said rotor can be actuated by motor means with—in addition to relatively slow motion for agitation in the position with the axis of rotation roughly horizontal, and in addition to intermittent motion in the position with the axis of rotation vertical for consecutive positioning of the test tubes in the reading station—relatively fast motion as well in order to obtain a centrifugation effect in the contents of the test tubes and therefore accelerated sedimentation, after the agitation stage and before the reading stage; moreover, in the vertical position of said axis of rotation, the test tubes are oriented, on said rotor, with their bottom facing outwards during the fast rotation for centrifugation.

According to one possible embodiment, said seats for the test tubes are fixed on the rotor and oriented with an angle of the order of 45° in relation to the axis of rotation of the rotor, with the bottom of the test tubes further than their mouth from the axis of rotation.

According to another possible embodiment, each of said seats for the test tubes oscillates on the rotor about a tangential axis and tends to adopt, by gravity, a position parallel to the axis of rotation of the rotor when the latter is vertical and moved in order to bring the test tubes consecutively to the reading station; on the other hand, the seats and the test tubes adopt, by centrifugal effect, an inclined position during fast rotation, until they are orthogonal to said axis of rotation of the rotor.

In practice, in order to keep the test tubes in the inclined position with the bottom oriented upwards, it is possible to provide, on the oscillating assembly, a guide member along the upper trajectory of the test tubes in the position of the rotor with the axis of rotation essentially horizontal in the agitation stage. Said guide member can be moved by an actuator in order to adopt a rest position in all stages with the exception of the agitation stage.

In the centrifugation stage, the rotor can be actuated with relatively fast motion, in particular of the order of 300 revolutions per minute.

The optical reading means also comprise, on a slide capable of sliding parallel to the test tube in the reading position, reading means for bar-codes or similar, which may be present on the individual test tubes, as well as means of reading the liquid by transparency.

BRIEF DESCRIPTION OF THE DRAWINGS

The invention will be better understood by following the description and the attached drawing which shows a non-limiting practical embodiment of the invention and in which:

FIG. 6 shows a partial view similar to FIG. 5, in which the section is taken along a vertical plane rotated by 90° in relation to the plane in FIG. 5;

FIG. 7 shows a partial view of the apparatus sectioned along a plane on line VII—VII in FIG. 6;

FIG. 8 shows a concise view, similar to that in FIG. 5, with the rotor in the position for carrying out the agitation stage;

DETAILED DESCRIPTION OF PREFERRED EMBODIMENTS

Figure 1:
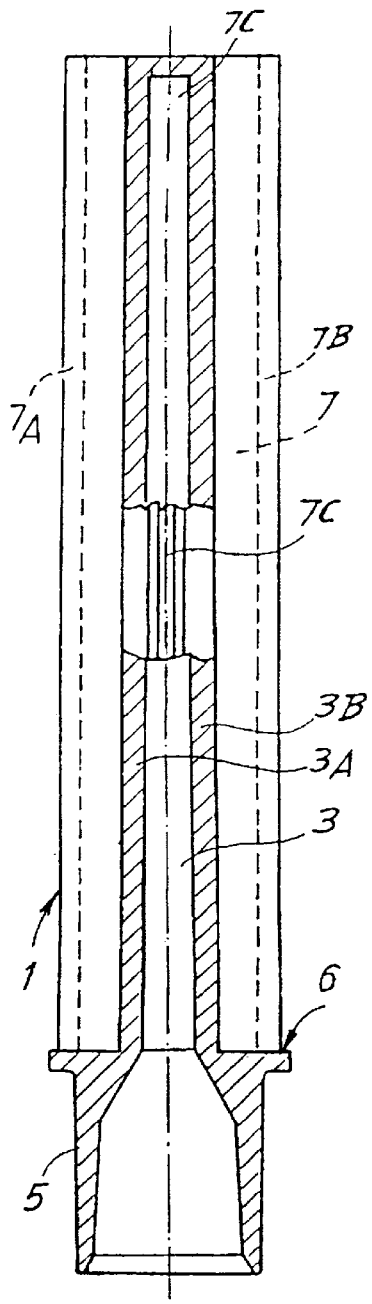
FIGS. 1 and 2 show front and lateral views respectively of an example of a test tube capable of being used with the analysis apparatus according to the invention, in partial section.
Figure 2:
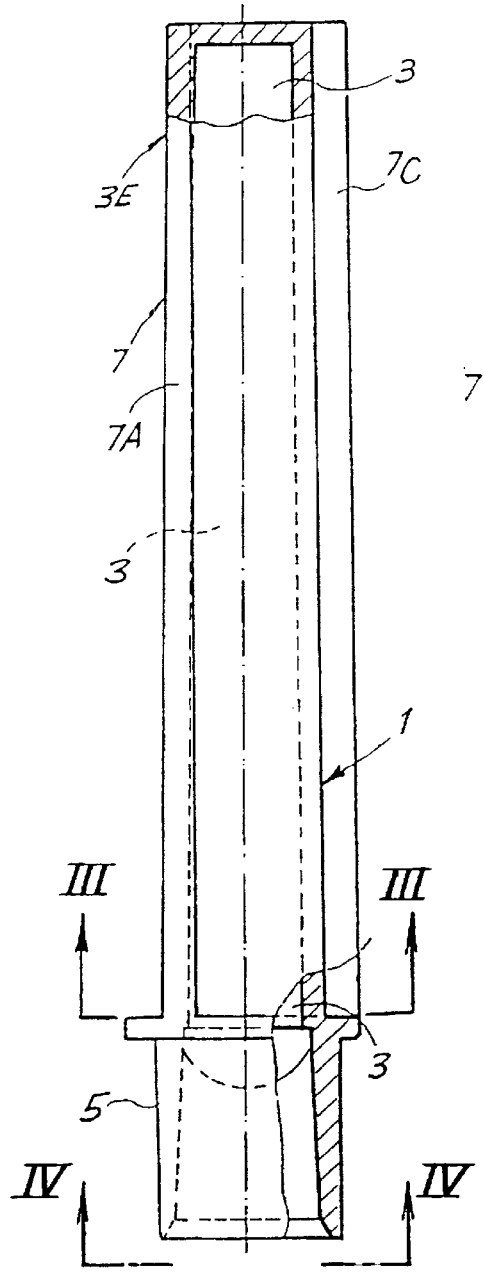
Figure 3:
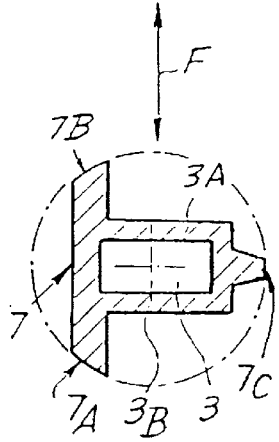
FIGS. 3 and 4 show views of the test tube sectioned along transverse planes on lines III—III and IV—IV in FIG. 2.
Figure 4:
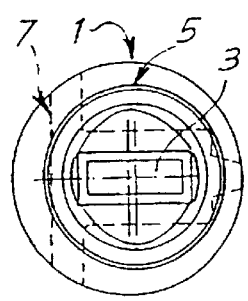

With reference to FIGS. 1 to 4, the test tube 1 comprises a container body with an essentially prismatic cavity 3 of essentially rectangular section and with a cylindrical connection 5 for filling and closure by means of a stopper which is not shown in the drawing. Along the long sides of its own section, the prismatic cavity 3 has flat walls 3A, 3B (FIGS. 1 and 3) of a thickness which is approximately constant apart from a slight variation for the dimension of cavity 3 for extraction of the test tube from the production mould, the test tube preferably being moulded in transparent plastic material. These walls 3A, 3B are intended to be passed through orthogonally, according to arrows F (FIG. 3), by the light rays of an electro-optical analysis apparatus.

The test tube also comprises a flat laminar zone 7 formed as an extension of one of the walls of said cavity 3 parallel to the direction F of the rays of the optical analysis system. This flat laminar zone 7 is capable of accommodating indications which can be read using reading means of, for example, optical type, such as bar-codes or equivalent. Advantageously, said laminar zone 7 is formed symmetrically on opposite sides of the essentially prismatic cavity.

In a preferred embodiment, the longitudinal edges 7A, 7B of said laminar zone and a further longitudinal projection 7C at a distance from said edges define the shape of the test tube so as to make it possible to center the test tube in a cylindrical housing. Said longitudinal projection 7C can be formed along a plane of symmetry orthogonal to said laminar zone 7. These characteristics make it possible to achieve effective centering of the test tube in seats provided in the analysis apparatus.

In any case, the test tube offers the possibility of using a large flat surface 7 for accommodating bar-codes and/or other useful data for the operations for which the test tube is used.

In FIGS. 5 to 8, an example of analysis apparatus according to the invention is illustrated. This comprises a support structure 103 (FIG. 5) equipped with a base 101 and with a hinge support 103A defining a horizontal axis X—X for an assembly 104 which can rotate about said axis X—X to adopt two end positions, as will be described below.

Said assembly 104 comprises a disc 107 and a rotor 106 which is capable of being inclined about an axis of rotation Y—Y orthogonal to said horizontal axis X—X. The rotor 106 comprises a disc 111 which is keyed coaxially onto a bush 111A which is rotatable, by means of bearings 109, about a shaft 105. The lower part 111B of the bush 111A is externally toothed in order to receive, by means of a toothed drive belt 113, the movement provided by a step motor 115. An annular disc 117, on the periphery of which notches cut in radially are provided for reading the angular position of the rotor by means of a double optical position sensor 119 supported, by means of a bracket 119A, by the support disc 107, is mounted below the rotatable disc 111 and coaxially therewith.

The rotor 106 also comprises a ring of seats 121 (in particular for test tubes such as those in FIGS. 1 to 4) which are fixed or formed peripherally on said disc 111 and arranged in such a manner that the test tubes 1, when inserted in the seats 121, are arranged and oriented symmetrically about said axis of rotation Y—Y with an inclination of approximately 45°, and with their bottom facing downwards and outwards in relation to said axis of rotation Y—Y, in the respective diametral plane and in the vertical position of said axis Y—Y. Each seat 121 for a test tube comprises a front plate 121C in which a hole is formed for the introduction of the test tube and to which a leaf spring 123 is fixed. Each seat 121 also comprises a cradle part 121A which is formed with essentially the same length as the test tube 1 and is capable of receiving the longitudinal edges 7A, 7B of the flat surface 7 of the test tube. The spring 123 acts on the test tube to hold it in bearing contact inside the cradle 121A. On the periphery of the through-hole of the plate 121C, a notch 121D is formed, which is capable of allowing the passage, with slight play, of the ridge 7C of the test tube for positioning the test tube angularly about its own axis. With this arrangement, once the test tube 1 has been inserted so that one of its edges 6 (FIG. 1) bears against the plate 121C, it is accurately positioned in relation to the rotor 106.

In the cradle 121A, a longitudinal opening 121B (FIG. 7) is formed, which leaves the view of the flat surface 7 of the test tube 1 clear, on which surface a bar-code and/or other indications are present, which can be read automatically.

Figure 5:
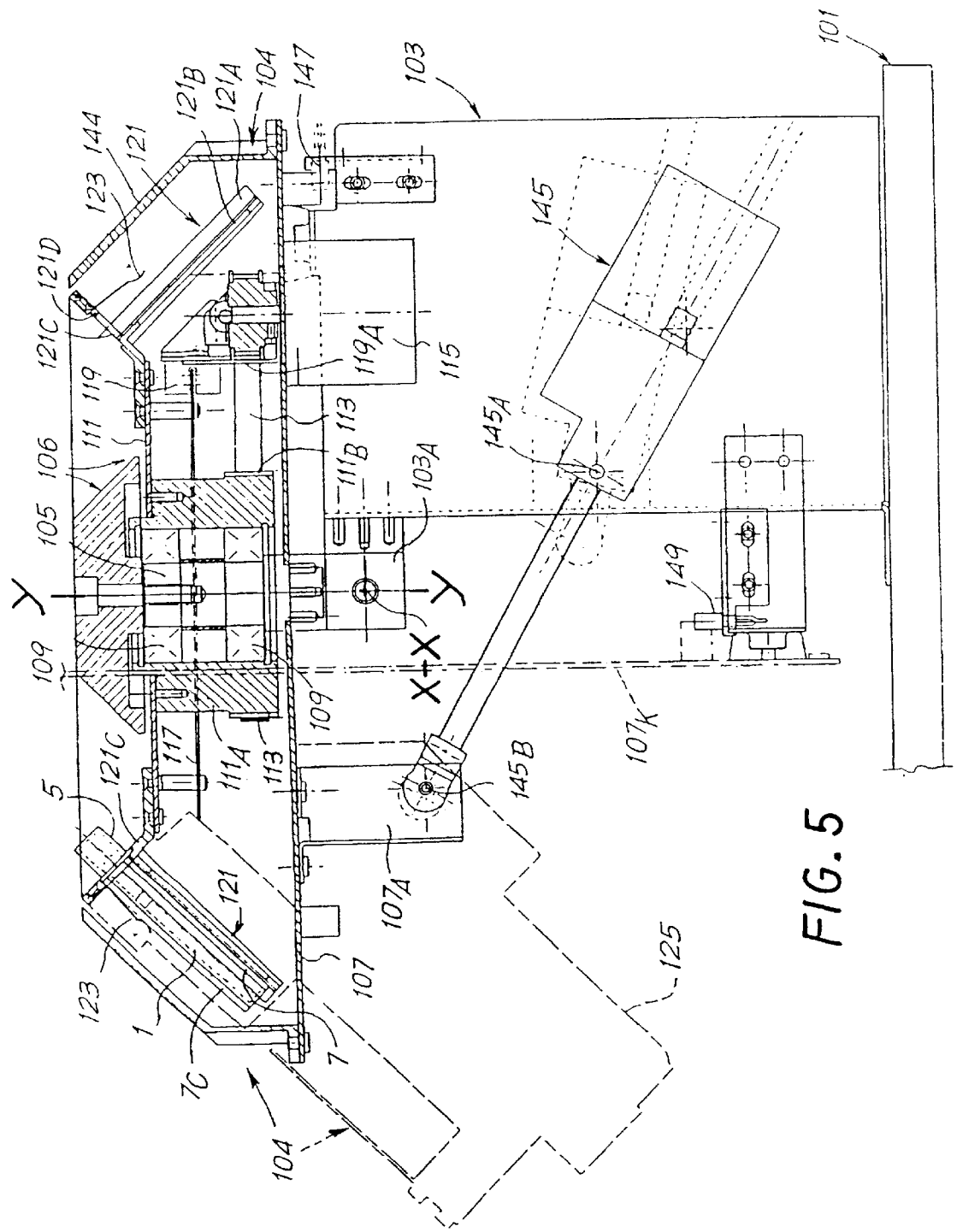
FIG. 5 shows a lateral view of a first example of an apparatus according to the invention, in which use can be made of a test tube as illustrated in the preceding figures.

A reading unit 125 (FIG. 6) is fixed to the support disc 107 in a position rotated by 90° in relation to the plane in FIG. 5; in FIG. 5, the space which said reading unit 125 occupies in relation to the support disc 107 is indicated by way of demonstration. The reading unit 125 comprises a pair of cylindrical guides 127 for a slide 129, said slide having the shape of an essentially parallelepipedal block. The guides 127 are fixed to the support disc 107, by means of brackets which are not shown in the drawing, with the same inclination as the test tubes, in other words approximately 45° in relation to the Y—Y axis. Running parallel to the guides 127 is one strand of a toothed belt 130 which is fixed to the slide 129 by means of a plate 131 and screw fastening means (not shown); a step motor 133 with a toothed pulley, fixed to the support disc 107 by means of a bracket 133A, and a return pulley 135 make it possible to move the slide 129 along the guides 127.

Two square profiles 137, 139 are fixed to the slide 129, which are parallel to one another and to the guides 127. An emitter/sensor pair 141A–141B and a bar-code reader 143 are fixed respectively to the free ends of said square profiles. The mutual spacing of the squares 137, 139 is such that it is possible to receive between them a test tube 1 inserted in a cradle 121; the emitter 141A and the detecting sensor 141B are positioned on opposite sides and close to the walls 3A, 3B of the test tube 1 while the bar-code reader 143 is positioned to read the codes present on the flat surface 7 of the test tube 1 through the longitudinal opening 121B.

By virtue of the movement of the slide 129 brought about by the motor 133, it is possible to make said emitter/sensor pair 141A–141B slide along the test tube located in the reading station in order to read the transparency of the liquid contained in the test tube and its variation along the test tube. The bar-code reader 143 serves to read what appears on the surface 7 of the test tube. When reading has been carried out, the slide 129 is returned to its lower position, in which said reading members 141A, 141B and 143 are moved out of the way of the test tube 1 and the cradle 121; in this position, it is possible to rotate the disc 111 of the rotor 106 to bring a consecutive test tube into position for a new reading cycle.

A protective casing 144, which encloses the rotor 106 and the seats 121 with any test tubes inserted, is fixed to the support disc 107 of the assembly 104. The casing can be removed and can have an opening for loading and removal of the test tubes. Alternatively, it is possible to mount on the rotor 106 a tray with seats for the test tubes, which can be replaced by another equipped with a new set of test tubes at the end of the cycle.

The assembly 104 can be rotated by 90° about the axis X—X by means of an actuator 145 articulated at 145A on the vertical support structure 103 and at 145B on a bracket 107A fixed to the support disc 107. Two proximity sensors 147, 149 are fixed to said support structure 103 to detect the presence of the disc 107 in a first position of the rotor 106 with the axis of rotation Y—Y arranged vertically (FIGS. 5 and 6) and, respectively, in a second position, indicated by 101K in FIG. 8 and in indicative lines by 107K in FIG. 5, in which said axis of rotation Y—Y is horizontal.

For the preparation and the automatic detection of the analysis parameters, the apparatus is equipped with an electronic control unit (not shown) which, once the test tubes 1 have been loaded into the seats 121, automatically carries out a predetermined analysis cycle.

The cycle comprises a first stage of agitation of the organic liquid in the test tubes, which is achieved by making the rotor 106 rotate slowly about its own axis Y—Y in, said second position of the assembly 104 with the axis Y—Y horizontal; in this manner, since the test tubes are inclined at 45° in relation to the axis Y—Y, these are oscillated twice on each revolution of the rotor, the contents consequently being agitated and thoroughly mixed. The assembly 104 is then rotated about the horizontal axis X—X until it is in said first position with the axis Y—Y vertical; in this position, the rotor is rotated at relatively high speed, for example 300 revolutions per minute, for a predetermined time to centrifuge the test tubes, bringing about rapid sedimentation of their contents. This stage is followed by a reading stage, in which, by means of partial rotations of the rotor on its vertical axis Y—Y, the various test tubes are brought, one after another, in front of the reading unit 125 to read the transparency of the liquid contained in the test tube and the bar-code of the test tube.

According to the variant shown in FIGS. 9 to 13, the members which are identical or correspond to those of the solution in FIGS. 5 to 7 have been increased by a hundred and, where corresponding members are different, a specific description is given below.

Figure 9:
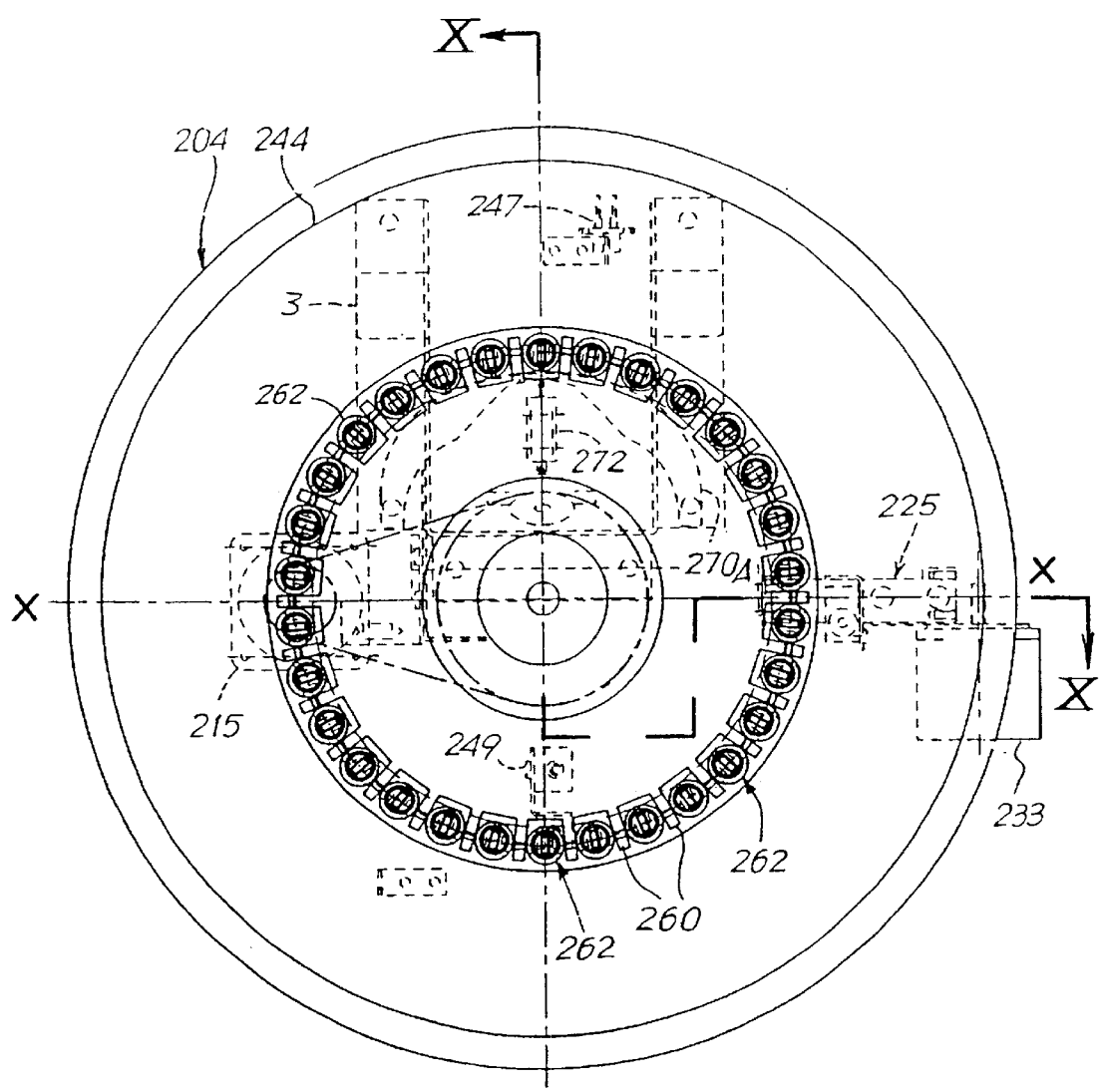
FIGS. 9 and 10 show a second example of an apparatus according to the invention in a diagrammatic plan view and in the section X—X in FIG. 9, in reading position, and, in broken lines, in the centrifugation position.
Figure 10:
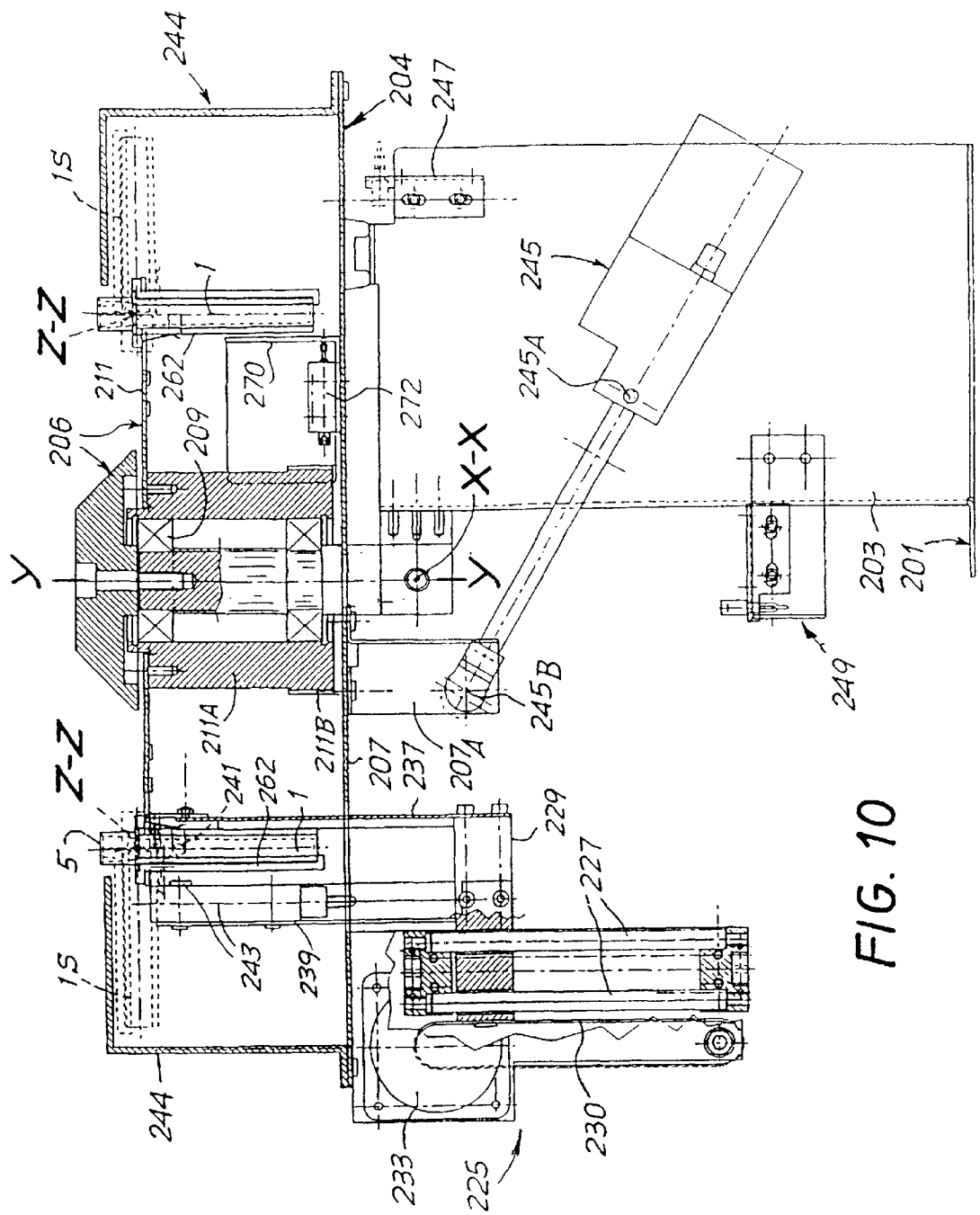
Figure 11:
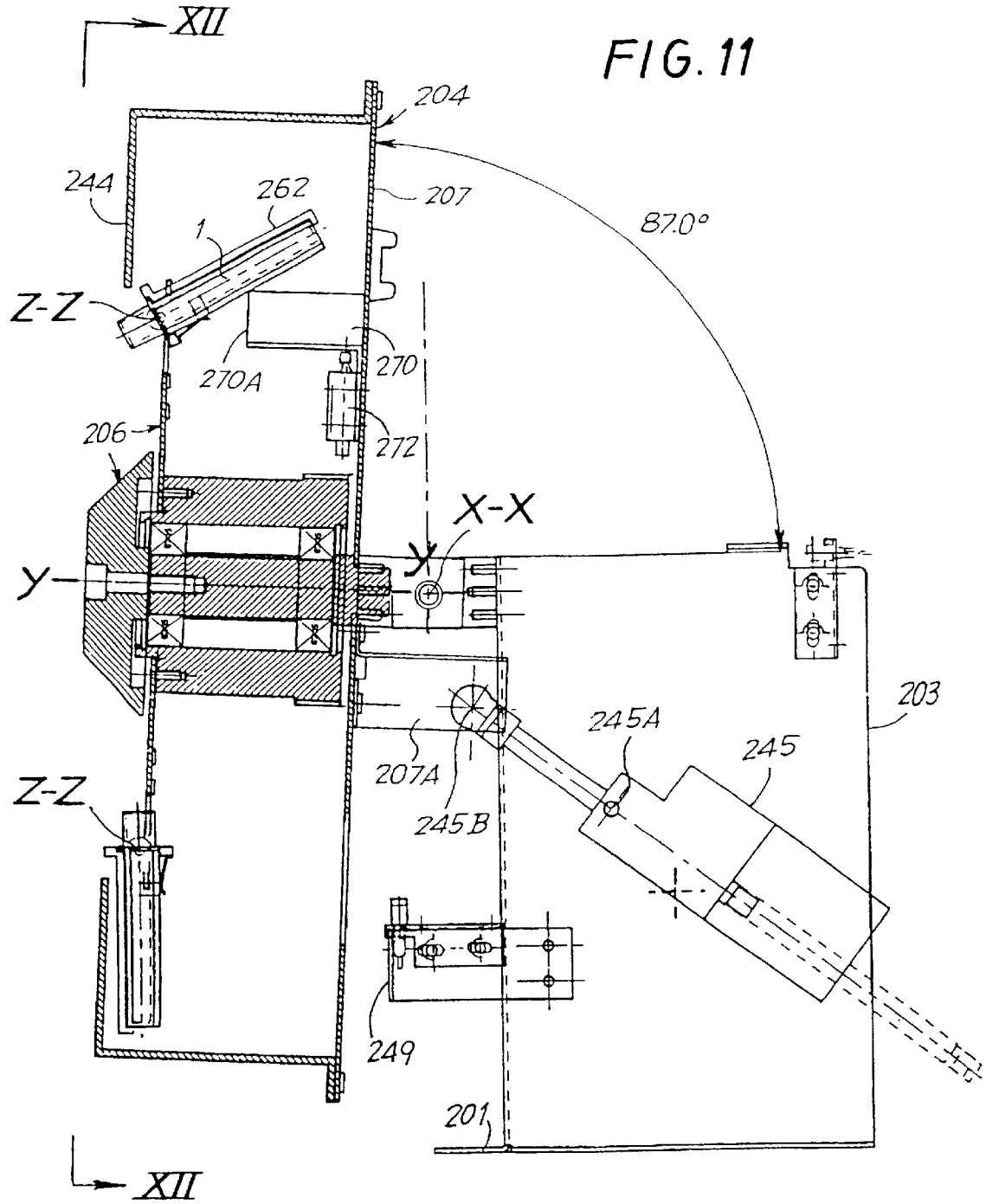
FIG. 11 is similar to FIG. 10 but shows the position for agitation of the test tubes.
Figure 12:
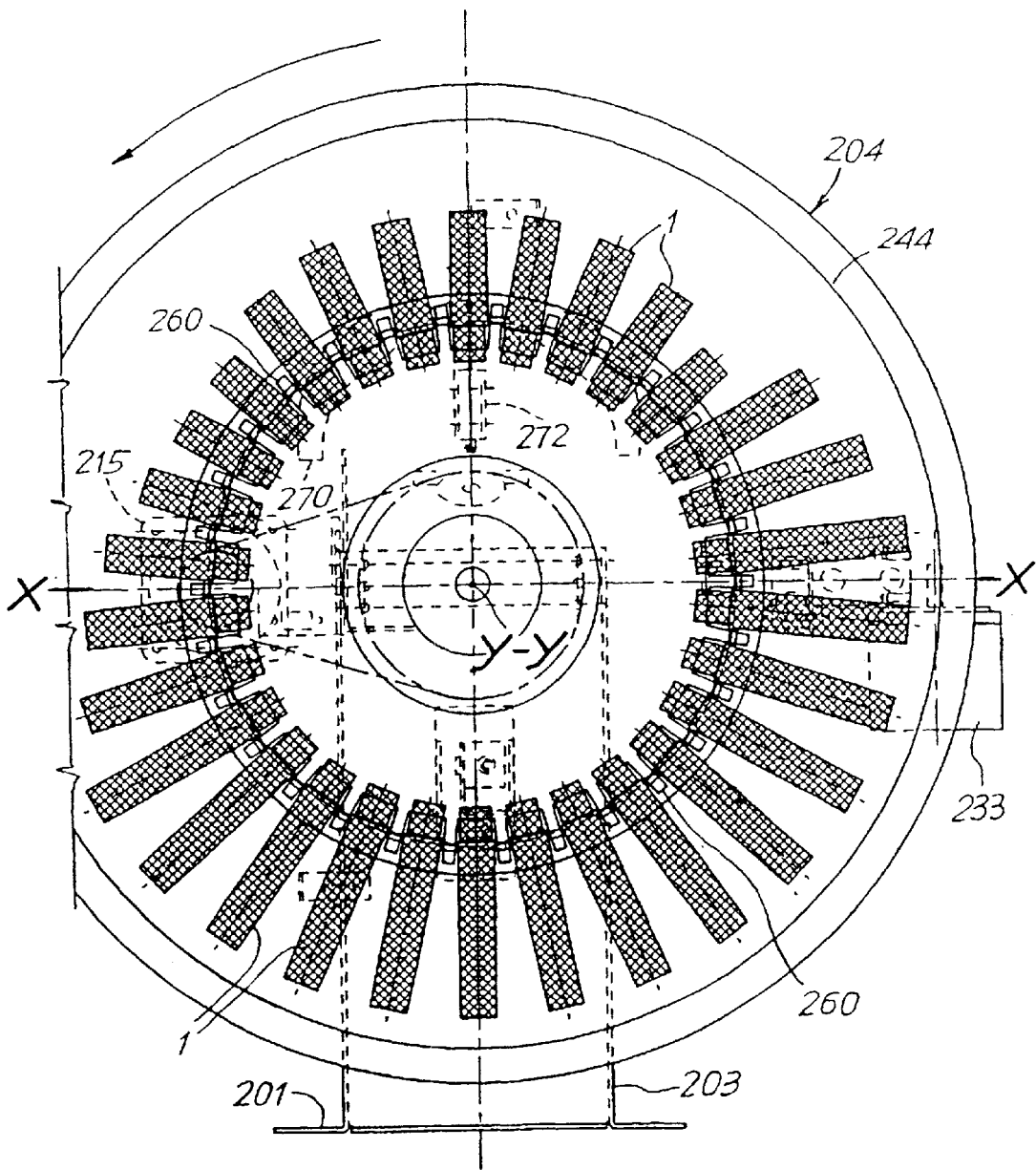
FIGS. 12 and 13 show a view along XII—XII in FIG. 11 and a detail of this with parts removed.
Figure 13:
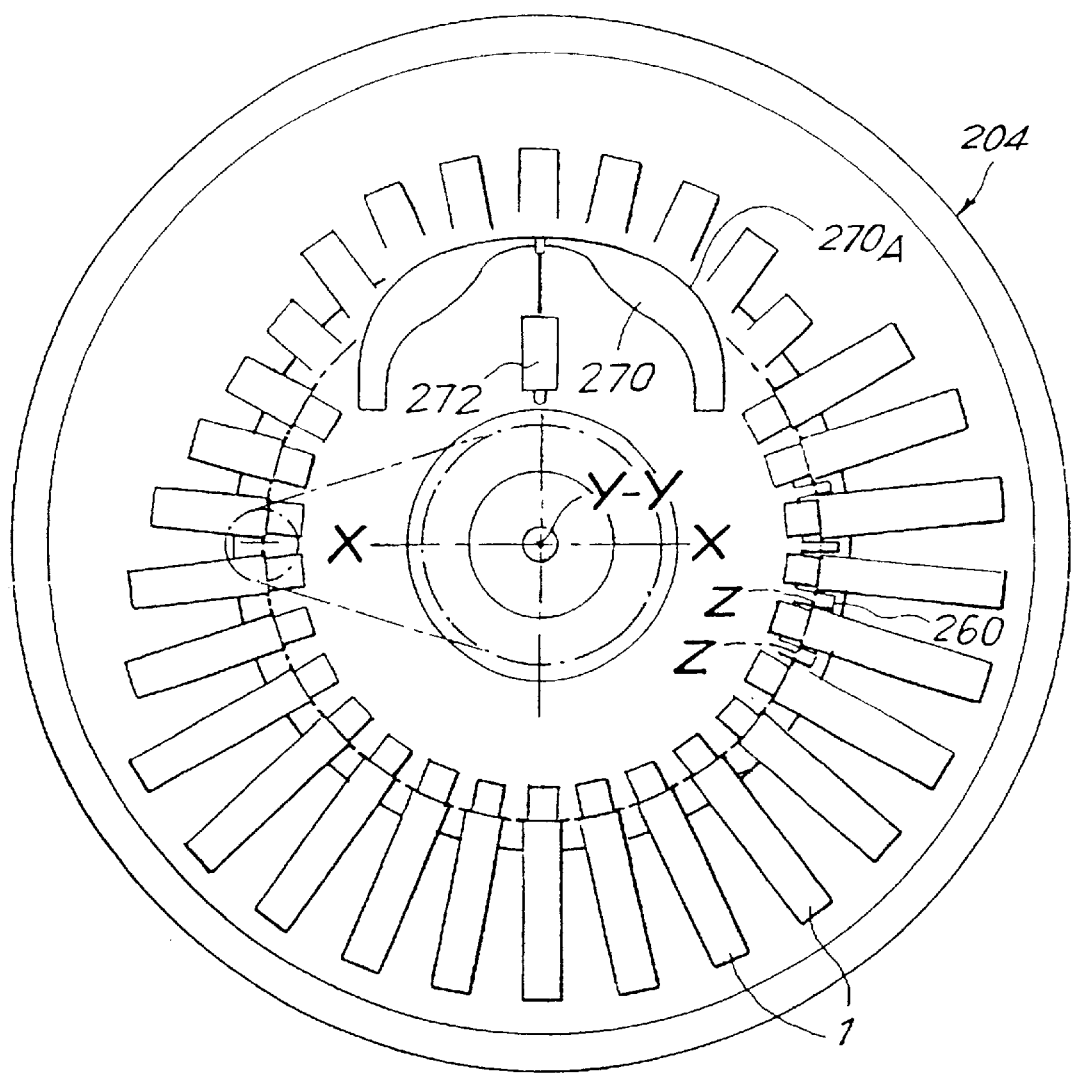

On the disc 211 of the assembly 206 which is capable of rotating about the axis Y—Y, supports 260 are provided peripherally for articulating, about tangential axes, individual test-tube holders 262 which therefore oscillate about respective tangential axes Z—Z; the test-tube holders 262 replace the seats 121 in the preceding example and are therefore mobile about the axes Z—Z instead of being fixed and oriented at approximately 45° as in the preceding solution. The individual test-tube holders 262 are capable of moving angularly between a radial position and a parallel position in relation to the axis Y—Y as can be seen in the various positions adopted by the test-tube holders and the test tubes as illustrated in the drawing; the oscillations take place within the protective casing 244 and orientation towards the position parallel to the axis Y—Y takes place by movement of said test-tube holders 262 towards the support disc 207. Unlike the preceding solution, the assembly 204 (which can move about the axis X—X) can adopt a position with the axis Y—Y vertical as shown in FIGS. 9 and 10 and an inclined position as shown in FIG. 11, in which the axis Y—Y is virtually horizontal but has undergone travel (in relation to the vertical position in FIGS. 9 and 10) through an angle of slightly less than 90° (for example 87°), as a result of which the support disc 207 is slightly inclined in relation to the vertical as shown in FIG. 11. The sensors 247 and 249 are arranged in such a manner that the two above-mentioned positions (horizontal and virtually vertical) can be adopted by the assembly 204.

In the zone of the trajectory of the rotor 206, which is towards the top in the position which the assembly 204 adopts according to FIG. 11, a guide member 270 is provided, which is shaped with an active profile 270A which is convex (FIGS. 12 and 13) towards the outside, said guide member 270 being movable in a radial direction of symmetry by means of an actuator 272 which can move said guide member 270 and its active profile 270A between a position close to the axis Y—Y and a more distant position in relation to the axis Y—Y when the assembly 204 is moved with the axis Y—Y close to the horizontal. The function of the guide member 270 is to modify the spontaneous position of the oscillating test-tube holders 262 (and therefore of the test tubes 1 accommodated in these) when the assembly 204 is arranged with the axis Y—Y virtually horizontal and slightly inclined in relation to the horizontal as shown in FIG. 11. Looking at FIG. 11, the freedom of movement of the test-tube holders 262 tends to keep the test tubes 1 vertical with their bottom facing downwards during the relatively slow rotation of the rotor 206 about the axis Y—Y. To carry out the stage of agitation of the liquid in the test tubes, as each test tube is gradually lifted, by the rotation about the axis Y—Y, from the position spontaneously adopted in the lower part of the trajectory as shown in FIG. 11, the test tubes tend to move, approximately halfway along the lifting trajectory, until they are in a position virtually parallel to the axis Y—Y. In this state, the individual test tubes come up against the active profile 270A of the guide member 270 which has moved into the more distant position in relation to the axis Y—Y; in this manner, the active profile 270A comes into contact with the individual test tubes, or with their test-tube holders 262, causing an inclination towards the periphery of the assembly 204 and towards the periphery of the rotor, thus subjecting the test tubes to a relatively marked inclination of the bottom of the test tube upwards as shown in FIG. 11. With the subsequent return of the test tubes towards the bottom, these progressively leave the profile 270A of the guide member 270 and return spontaneously to the position oriented towards the bottom in the lower zone of the slow agitation trajectory of the rotor about the axis Y—Y in the virtually horizontal position. The agitation stage is consequently achieved, which is equivalent to that achieved in the preceding solution with the test tubes positioned rigidly at a defined angle (approximately 45° or another angle). In fact, the movements which each test tube carries out on each revolution about the axis Z—Z in the agitation stage are more effective than those achieved in the test tubes using the preceding solution.

When the assembly 204 is brought into the position in FIG. 10, that is to say with the axis Y—Y vertical, the guide member 270 is returned by the actuator 272 to a position close to the axis Y—Y and therefore to the core 211A, as a result of which this guide member 270 no longer interferes with the test tubes which spontaneously adopt the vertical position oriented downwards through the effect of gravity and of the freedom of oscillation of the test-tube holders 262. With the slow intermittent movements of the rotor 206, the individual test tubes can in this state be positioned in the reading station to be read by the sensors 241 and 243 for the optical examination of the liquids contained in the test tubes and for reading the codes along the support surfaces exposed to reading by the sensors 243.

When the stage of sedimentation accelerated by centrifugal effect is to be carried out, the test tubes tend to move, through the effect of centrifugal force, about the axes Z—Z from the vertical position facing downwards achieved spontaneously by gravity until they are in a horizontal position with their bottom facing outwards, as indicated in broken lines by 1S, to achieve sedimentation accelerated by the centrifugal effect. After centrifugation, by stopping or in any case slowing the rotation of the rotor 206 about the axis Y—Y which is still in the vertical position, the test tubes return from the radial position 1S to the vertical downward position in a state in which they can be subjected to reading by the reading assembly 225.

It is intended that the drawing only shows an exemplary embodiment which is given solely by way of practical demonstration of the invention, it being possible for the invention to vary in form and arrangement without moreover leaving the scope of the idea which forms the invention itself. Any presence of reference numbers in the enclosed claims has the purpose of facilitating reading of the claims with reference to the description and to the drawing, and does not limit the scope of protection represented by the claims.

What is claimed is:

1. Apparatus for preparation and performance, in times of less than 10 minutes, of analysis of a sedimentation velocity type on liquids which have to be agitated in test tubes, comprising: an assembly, on a base structure, which assembly oscillates about a horizontal oscillation axis between two limit positions, a rotor on said assembly, which rotor is capable of rotating about a rotation axis orthogonal to said horizontal axis a ring of seats for test tubes on said rotor, which seats are arranged symmetrically about said rotation axis, means of moving said assembly into a position with the rotation axis substantially horizontal to perform agitation when said rotor is rotated, and into a position with the rotation axis vertical to carry out a reading stage, optical reading means, in a reading station, for optical reading along the test tube which arrives in said station by intermittent movements of said rotor when it is arranged with the rotation axis oriented vertically each of said seats for the test tubes have a connection which oscillates on the rotor about a tangential axis and tends to adopt, by gravity, a position parallel to the rotation axis of the rotor when the latter is vertical and moved in order to bring the test tubes consecutively to the reading station, the seats and the test tubes adopting, by centrifugal effect, an inclined position during fast rotation, until they are even orthogonal to said rotation axis; in that on the oscillating assembly, guide members connected to said assembly and movably positioned on said assembly to contact the test tubes along an upper trajectory of the test tubes in the position of the rotor with the rotation axis essentially horizontal, during agitation, to put the test tubes in an inclined position with their bottom facing upwards; and in that said rotor is rotatable by motor means at an agitation speed for agitation of the fluid with the rotation axis horizontal, and in addition to intermittent motion in the position with the axis of rotation vertical for consecutive positioning of the test tubes in the reading station, said motor means rotating said rotor at a centrifugal speed with said rotation axis substantially vertical in order to obtain a centrifugation effect in the liquid of the test tubes and therefore accelerated sedimentation, after agitation and before the reading stage.

2. Apparatus according to claim 1, wherein:

a guide actuator moves said guide members into a rest position away from the test tubes during rotation of said rotor at said centrifugal speed and during said intermittent motion, said seats on said rotor are in a vertical position during reading of the test tubes.

3. Apparatus according to claim 1, wherein:

said centrifugal speed of said rotor is faster than said agitation speed and is substantially 300 revolutions per minute.

4. Apparatus according to claim 1, wherein:

said optical reading means are borne by said assembly.

5. Apparatus according to claim 1, wherein:

said optical reading means also comprise, on a slide capable of sliding parallel to the test tube, reading means for bar-codes on the individual test tubes.

6. The apparatus in accordance with claim 1, wherein:

said connection of said seats cooperate with gravity to position a longitudinal axis of the test tubes substantially orthogonal to said rotation axis during rotation of said rotor at said centrifugal speed.

7. An apparatus in accordance with claim 1, wherein:

said reading station includes a sensor for measuring a transparency of the liquids in the test tubes.

8. An apparatus in accordance with claim 1, wherein:

said reading station includes a sensor for measuring a sedimentation rate of the liquids in the test tubes.

9. An apparatus in accordance with claim 1, wherein:

said connection of said seats cooperate with gravity to position a longitudinal axis of the test tubes substantially vertical in said reading station.

10. An apparatus for analysis of sedimentation rate on agitated liquids in containers, the apparatus comprising:

a base structure;

an assembly pivotally mounted on said base structure about an oscillation axis between first and second positions;

a rotor rotatably mounted on said assembly about a rotation axis orthogonal to said oscillation axis;

a plurality of seats for receiving the containers, each of said seats having a tangential pivotal connection to said rotor for being pivotally connected to said rotor about a seat axis tangential to rotation of said rotor about said rotation axis;

an actuator moving said assembly and said rotor into said second position to have rotation of said rotor cause agitation of the liquids in the containers, said actuator moving said assembly and said rotor into said first position for measuring the sedimentation rate;

a reading station for optical reading along the containers;

a drive for rotating said rotor at an agitation speed when said assembly and said rotor are in said second position for agitating the liquids in the container, said drive rotating said rotor at a centrifugal speed when said assembly and said rotor are in said first position to accelerate sedimentation;

a guide member arranged on said assembly and movable into and out of contact with the containers to selectively oscillate the containers about said seat axis when said rotor is rotating in said second position.

11. The apparatus in accordance with claim 10, wherein:

said first position of said rotor and said tangential pivotal connection of said seats cooperate with rotation of said rotor and gravity to force sediment in the liquids to a bottom of the containers;

said second position of said rotor and said tangential pivotal connection of said seats cooperate with rotation of said rotor and gravity to agitate the sediment in the liquids.

12. An apparatus in accordance with claim 10, wherein:

said reading station includes a sensor for measuring a transparency of the liquids in the containers.

13. An apparatus in accordance with claim 10, wherein:

said reading station includes a sensor for measuring a sedimentation rate of the liquids in the containers.

14. An apparatus in accordance with claim 10, wherein:

said reading station includes a sensor for measuring Erytro Sedimentation Rate (E.S.R.) of the liquids in the containers.

15. An apparatus in accordance with claim 10, wherein:

said tangential pivotal connection of said seats cooperate with gravity to position a longitudinal axis of the containers substantially vertical in said reading station;

said tangential pivotal connection cooperates with gravity to pivot the containers between first and second pivot positions and about said seat axis during rotation of said rotor in said second position.

16. An apparatus in accordance with claim 15, wherein:

said first pivot position is substantially radially outward of said rotor;

said second position of said assemble holds said rotation axis angularly spaced from horizontal to cause said second pivot position of the containers to always be on a same axial side of said rotor.

17. An apparatus for analysis of sedimentation rate on agitated liquids in containers, the apparatus comprising:

a base structure;

an assembly pivotally mounted on said base structure about an oscillation axis between first and second positions;

a rotor rotatably mounted on said assembly about a rotation axis orthogonal to said oscillation axis;

a plurality of seats for receiving the containers, each of said seats having a tangential pivotal connection to said rotor for being pivotally connected to said rotor about a seat axis tangential to rotation of said rotor about said rotation axis, said second position of said assembly is arranged to cause said rotor to move the containers in a substantially vertical trajectory;

an actuator moving said assembly and said rotor into said second position to have rotation of said rotor cause agitation of the liquids in the containers, said actuator moving said assembly and said rotor into said first position for measuring the sedimentation rate;

a guide member arranged on said assembly and movable into contact with the containers along an upper portion of said vertical trajectory of the containers when rotating in said second position of said rotor, said guide member contacting the containers to oscillate the containers about said seat axis when said rotor is rotating in said second position;

a reading station for optical reading along the containers;

a drive for rotating said rotor at an agitation speed when said assembly and said rotor are in said second position for agitating the liquids in the container, said drive rotating said rotor at a centrifugal speed when said assembly and said rotor are in said first position to accelerate sedimentation.

18. An apparatus for analysis of sedimentation rate on agitated liquids in containers, the apparatus comprising:

a base structure;

an assembly pivotally mounted on said base structure about an oscillation axis between first and second positions;

a rotor rotatably mounted on said assembly about a rotation axis orthogonal to said oscillation axis;

a plurality of seats for receiving the containers, each of said seats having a tangential pivotal connection to said rotor for being pivotally connected to said rotor about a seat axis tangential to rotation of said rotor about said rotation axis;

an actuator moving said assembly and said rotor into said second position to have rotation of said rotor cause agitation of the liquids in the containers, said actuator moving said assembly and said rotor into said first position for measuring the sedimentation rate;

a reading station for optical reading along the containers;

a drive for rotating said rotor at an agitation speed when said assembly and said rotor are in said second position for agitating the liquids in the container, said drive rotating said rotor at a centrifugal speed when said assembly and said rotor are in said first position to accelerate sedimentation;

said oscillation axis of said assembly is substantially horizontal;

said first position of said assembly holds said rotational axis substantially vertical;

said second position of said assembly holds said rotational axis substantially horizontal and moves the containers in a vertical trajectory during rotation of said rotor in said second position;

said tangential pivotal connection of said seats cooperate with gravity to position a longitudinal axis of the containers parallel to said rotation axis in said first position of said assembly and said rotor when said rotor is stopped, and to incline the longitudinal axis of the containers to said rotation axis when said rotor is rotated at said centrifugal speed;

said drive rotates said rotor intermittently to bring the containers consecutively to said reading station when said rotor and said assembly are in said first position;

a guide member arranged on said assembly and movable into contact with the containers along an upper trajectory of the containers when rotating in said second position of said rotor, said guide member moving the containers into a position with a bottom of the containers facing upward;

said centrifugal speed is faster than said agitation speed;

said drive rotates said rotor at said centrifugal speed after rotation at said agitation speed and before said rotor brings the containers to said reading station;

said seats are arranged in a ring symmetrically about said rotation axis.

19. The apparatus in accordance with claim 18, wherein:

said tangential pivotal connection of said seats cooperate with gravity to position a longitudinal axis of the containers substantially orthogonal to said rotation axis during rotation of said rotor at said centrifugal speed in said first position.

* * * * *